(12) United States Patent
Marko-Varga et al.

(10) Patent No.: US 10,718,760 B2
(45) Date of Patent: Jul. 21, 2020

(54) METHOD FOR DRUG BINDING ANALYSIS IN A TISSUE SAMPLE

(71) Applicants: Treat4Life AB, Lund (SE); Anne-Sophie Rockborn Fehniger, Lund (SE)

(72) Inventors: Gyorgy Marko-Varga, Malmö (SE); Thomas Fehniger, Lund (SE); Yutaka Sugihara, Lund (SE)

(73) Assignee: TREAT4LIFE AB, Lund (SE)

( * ) Notice: Subject to any disclaimer, the term of this patent is extended or adjusted under 35 U.S.C. 154(b) by 262 days.

(21) Appl. No.: 15/777,651

(22) PCT Filed: Nov. 18, 2016

(86) PCT No.: PCT/EP2016/078131
§ 371 (c)(1),
(2) Date: May 18, 2018

(87) PCT Pub. No.: WO2017/085251
PCT Pub. Date: May 26, 2017

(65) Prior Publication Data
US 2018/0348210 A1     Dec. 6, 2018

(30) Foreign Application Priority Data
Nov. 20, 2015  (SE) ...................... 1551503

(51) Int. Cl.
*G01N 33/58* (2006.01)
*C40B 30/04* (2006.01)
(Continued)

(52) U.S. Cl.
CPC ......... *G01N 33/532* (2013.01); *A61K 31/437* (2013.01); *G01N 33/5082* (2013.01);
(Continued)

(58) Field of Classification Search
CPC ...... G01N 33/532; G01N 33/60; G01N 33/58; G01N 33/5082; G01N 33/574;
(Continued)

(56) References Cited

U.S. PATENT DOCUMENTS

| 2007/0122405 A1* | 5/2007 | Roschke | C07K 16/2866 |
| | | | 424/143.1 |
| 2009/0118135 A1* | 5/2009 | Reed | G01N 33/574 |
| | | | 506/9 |
| 2012/0157328 A1 | 6/2012 | Dudek et al. | |

FOREIGN PATENT DOCUMENTS

| WO | 1995011217 | 4/1995 |
| WO | 2013036885 A1 | 3/2013 |

OTHER PUBLICATIONS

Hefner G et al; ChemMedChem; 2009; vol. 4; pp. 1523-1528.
(Continued)

*Primary Examiner* — Jennifer Wecker
*Assistant Examiner* — Michael Paul Shimek
(74) *Attorney, Agent, or Firm* — Lowe Graham Jones PLLC

(57) ABSTRACT

A method of determining the specific binding of ligand reversibly binding to a binding site in a sample using displacement competitive inhibition. The method comprising incubating the ligand (unlabeled) in the absence of a labeled ligand on a first tissue specimen, incubating the ligand (unlabeled) in the presence of a labeled ligand on a second tissue specimen, the first and the second tissue specimens being adjacent sections of specimen. MALDI imaging mass spectrometry is used to subsequently visualizing bound ligand localization, using in the first and second tissue specimen, respectively.

15 Claims, 10 Drawing Sheets

(51) Int. Cl.
*A61K 31/437* (2006.01)
*G01N 33/532* (2006.01)
*G01N 33/50* (2006.01)
*G01N 33/574* (2006.01)
*G01N 33/68* (2006.01)
*G01N 33/60* (2006.01)
*H01J 49/00* (2006.01)

(52) U.S. Cl.
CPC ........... *G01N 33/574* (2013.01); *G01N 33/58* (2013.01); *G01N 33/60* (2013.01); *G01N 33/6851* (2013.01); *H01J 49/0004* (2013.01); *G01N 2800/52* (2013.01)

(58) Field of Classification Search
CPC ........... G01N 33/6851; G01N 2800/52; G01N 2458/15; A61K 31/437; H01J 49/0004
See application file for complete search history.

(56) References Cited

OTHER PUBLICATIONS

Lengqvist J et al; J. Mass Spectrom, 2005, vol. 40 pp. 1448-1461.
Niessen K V et al; ChemBioChem, 2005, vol. 6 pp. 1769-1775.
Kwon Ho Jeong et al "Drug compund characterization by mass spectrometry imaging in cancer tissue" Archives of Pharmacal Research, Natl. Fisheries University, Pusan, KR vol. 38, No. 9, Jul. 23, 2015 pp. 1718-1727.

* cited by examiner

 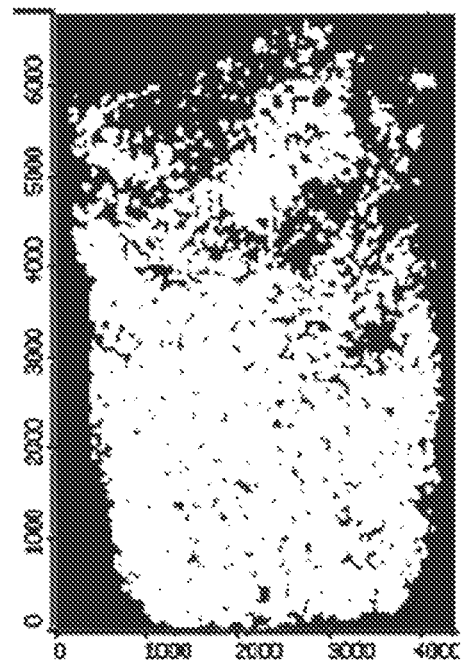
Fig. 7A　　　　　　　　　　　　Fig. 7B
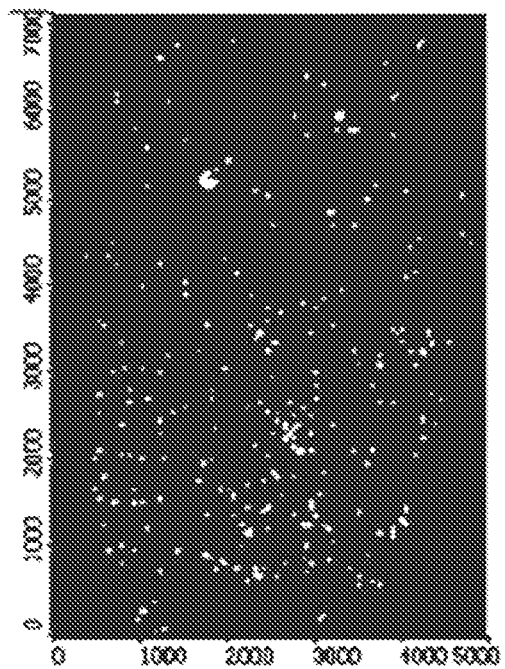 
Fig. 7C　　　　　　　　　　　　Fig. 7D

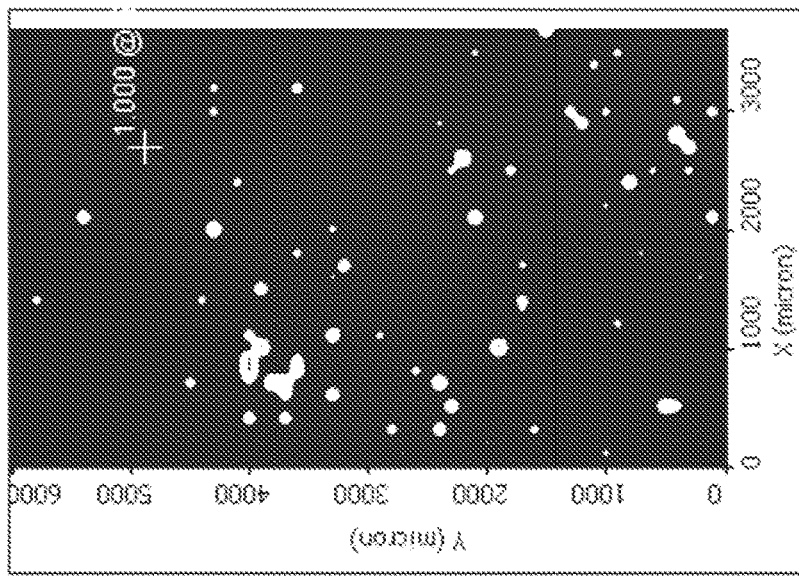
Fig. 8A  100 nM vemurafenib  m/z 383.1
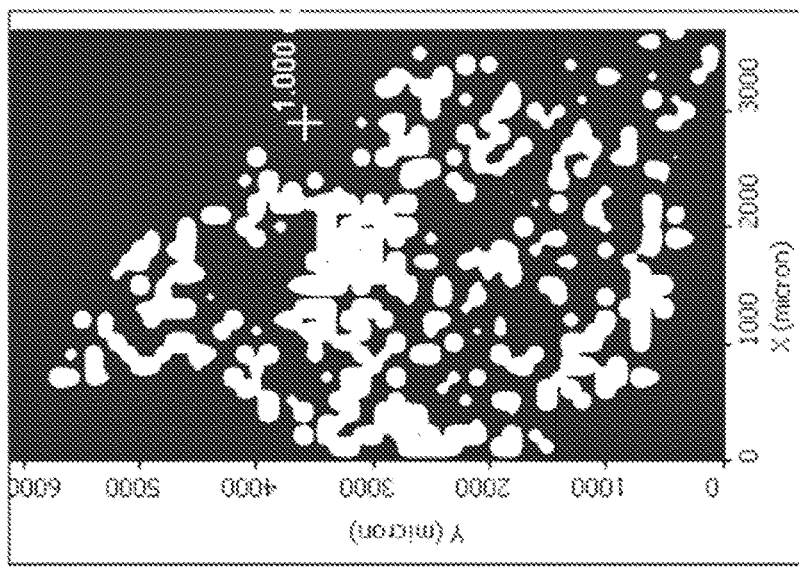
Fig. 8B  100 nM vemurafenib  m/z 383.1
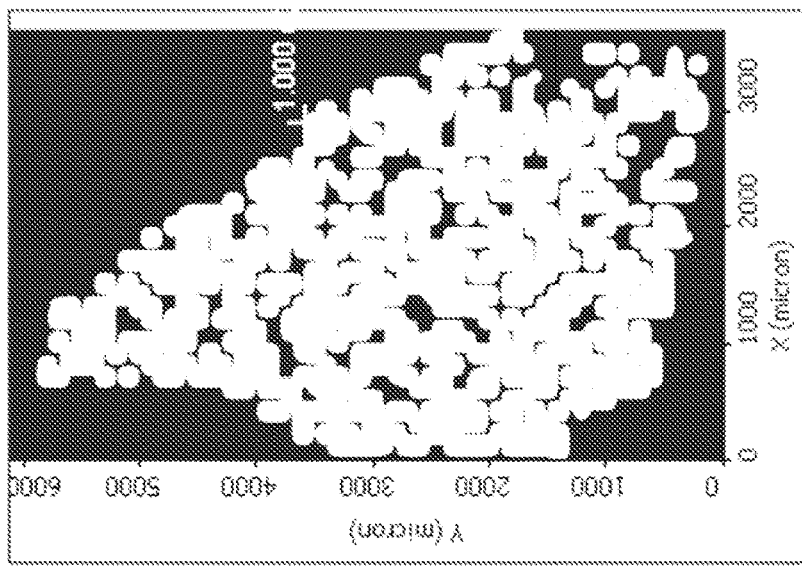
Fig. 8C  1 µM 13C vemurafenib  m/z 389.1

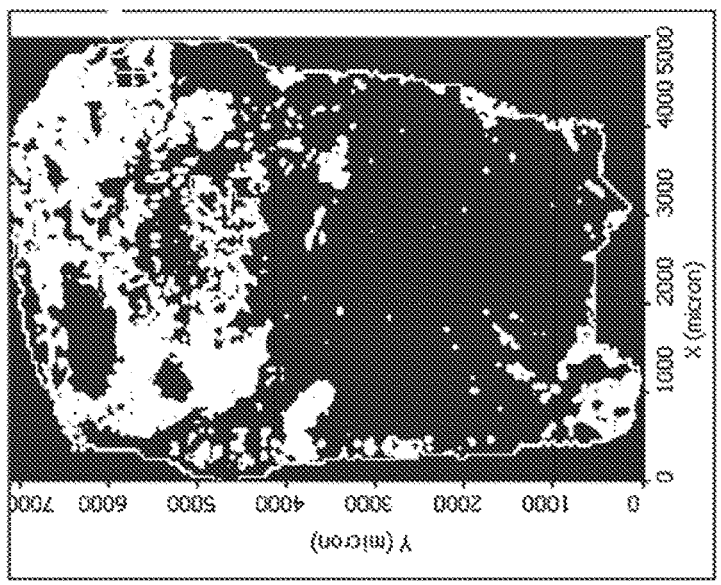
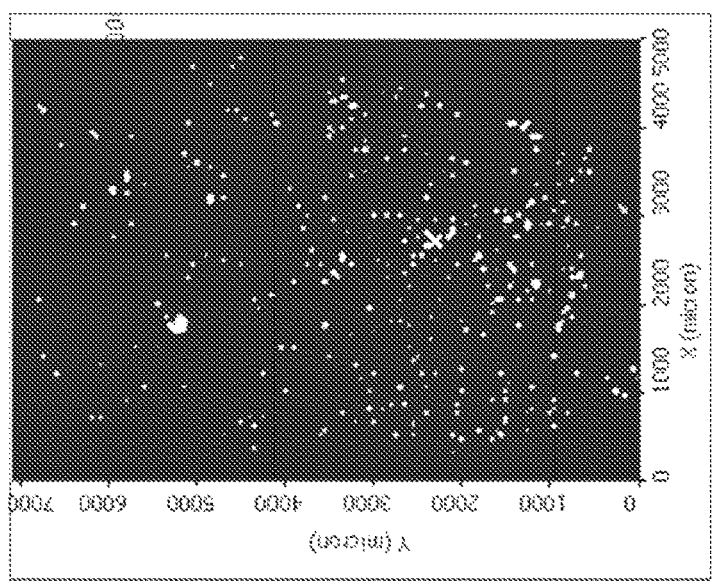
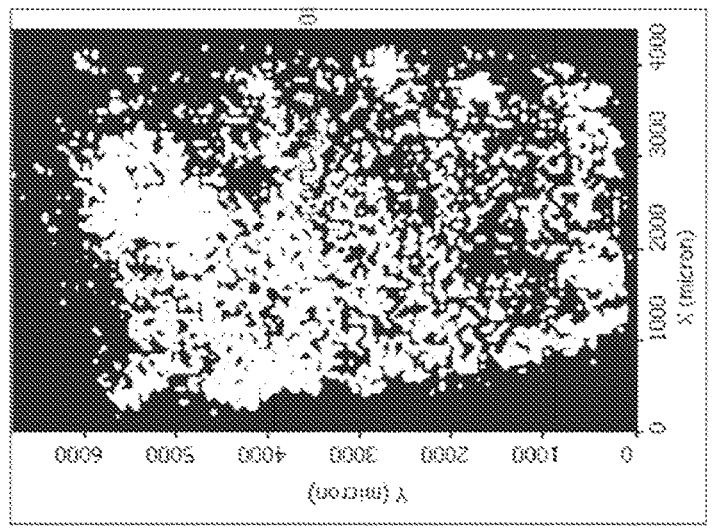
Fig. 9A  m/z 383.1  100 nM vemurafenib
Fig. 9B  m/z 383.1  100 nM vemurafenib
Fig. 9C  m/z 389.1  1 µM 13C vemurafenib

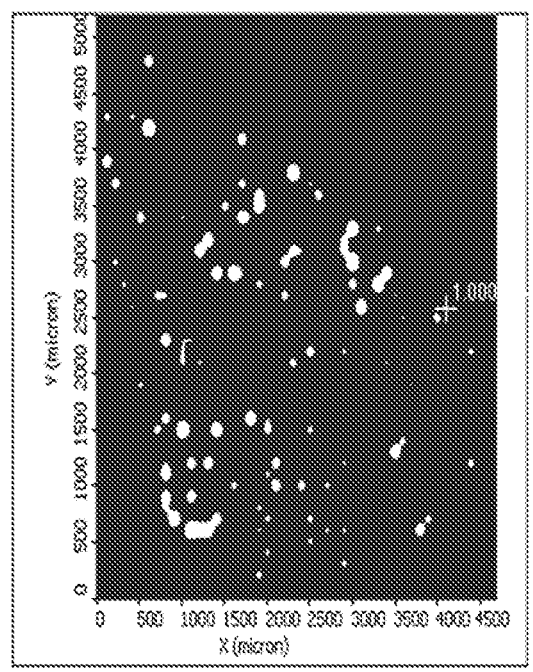
m/z 389.1  100 nM vemurafenib  Fig. 10A
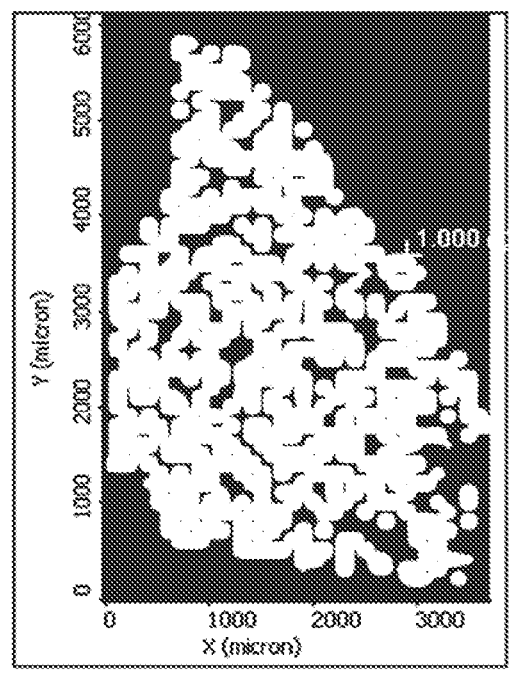
m/z 389.1  1 uM vemurafenib  Fig. 10B
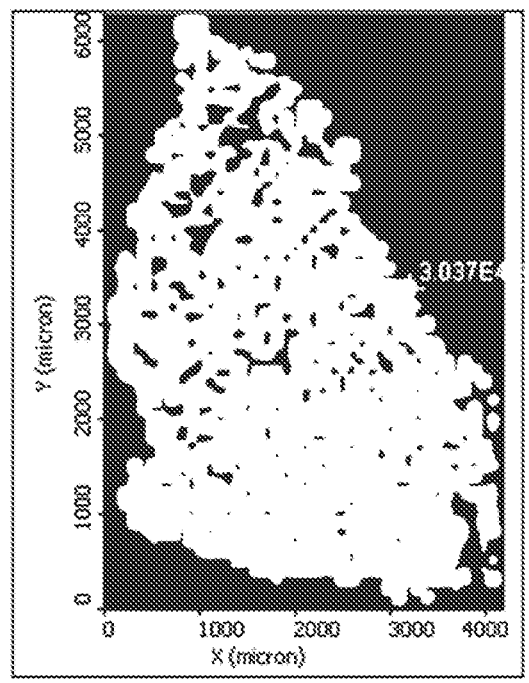
m/z 389.1  10 uM vemurafenib  Fig. 10C
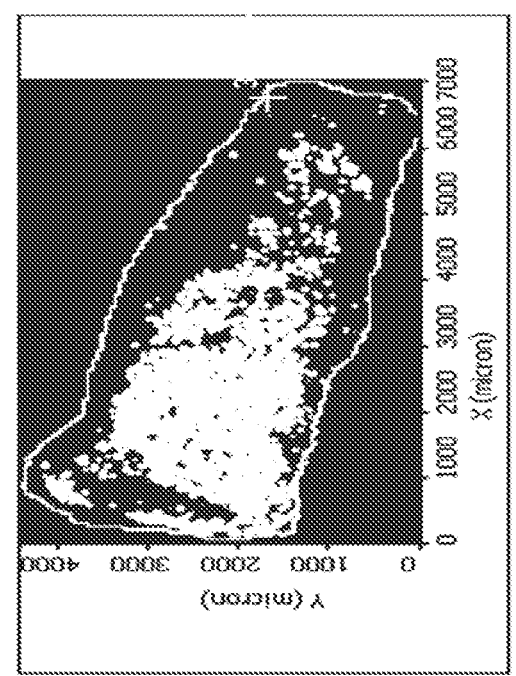
m/z 389.1  100 uM vemurafenib  Fig. 10D

METHOD FOR DRUG BINDING ANALYSIS IN A TISSUE SAMPLE

PRIORITY CLAIMS

This invention claims priority to PCT application Ser. No. PCT/EP2016/078131 filed Nov. 18, 2016, which claims priority to Swedish Application Serial No. 1551503-4 filed Nov. 20, 2015; the contents of which are hereby incorporated by reference.

FIELD OF THE INVENTION

This invention pertains in general to the field of mass spectrometry imaging. More particularly the method relates to the ability to analyze drug specificity and drug selectivity, in particular, the invention describes a multimodal method capable of determining the presence and localization of drug and metabolite(s) in patient samples by mass spectrometry imaging.

BACKGROUND OF THE INVENTION

It is known that the ever increasing demands in healthcare today posture high prospects and commands onto the research community to establish and come up with new solutions that can improve clinical outcome with improved cost efficiency.

In response to these challenges, modern healthcare is looking for ways to treat patients that are both more efficient and beneficial for the patient, as well as more cost saving. The introduction of regulatory directives are central to our research community in order to manage to meet the demands from e. g., cancer patients that are expecting drugs that are more safe, with lower mortalities, and with a fast onset of efficacy.

Thus, there is a need for new methods for diagnosis, enabling a physician both to diagnose disease and to manifest patient response to therapy.

Together with the National Cancer Institute, NIH and local clinicians and scientists there has been extensive progress made to work out and provide a Protein biomarker discovery and validation strategy. These regulatory guidelines provide high-quality standardized, sensitive, specific, quantitative, and readily accessible protein, peptide, or other biomarkers of health, disease, response to therapy into the approval processes of regulatory agencies (e.g., U.S. Food and Drug Administration; FDA). These developments are vital for healthcare professionals to improve diagnosis by the understanding mode-of-drug action mechanisms, detect cancers at an early stage, identify the likelihood of cancer recurrence, and stratify stages with differential survivals.

Cancer is also known as malignant neoplasm or pathological malignant tumor development. The cancer disease mechanisms involves an abnormal cell growth that will result in the invasion and most possible spread of these cancer cells to other parts of the organs and regions within the body. The most common and signs of symptoms usually includes abnormal bleeding, and/or lengthy cough, unexplained loss of weight and an alteration in bowel movements while these symptoms may indicate cancer, they may also occur due to other issues, and there can be hundreds of different known cancers that affect humans.

It is a well-known fact that the cause of about 22% of cancer deaths is due to tobacco use. Another 10% is due to overweight and obesity, a poor diet, and often a lack of physical exercise and over consumption of alcohol. Other factors include certain infections and/or exposure to infections and environmental pollutants. In the developing world close to 20% of cancers are due to infections such as Hepatitis B, Hepatitis C and human papilloma virus. These factors act, at least partly, by changing the genes and proteins of a cell. Typically many such genetic changes are required before cancer develops. Statistically, approximately 5-10% of cancers are due to genetic defects inherited from a person's parents.

The cancer spread and initiation phases of disease can be detected by certain signs and symptoms or diagnostic tests. It is then typically further investigated by various types of medical imaging platforms, such as X-ray, CT, PET, MRI or mass spectrometry imaging and confirmed by pathology diagnosis of a biopsy. The benefits of screening in breast cancer are valuable both for the patient as well as our society, as proven by the treatment of woman and breast cancer as well as for men with prostate cancer where in both diseases the diagnosis development has decreased the mortality rates significantly over the last decade.

Cancer is often treated with some combination of radiation therapy, surgery and/or chemotherapy. Lately, targeted therapy has been proven very efficient. The chance of survival depends on the type of cancer and the extent of disease at the start of any type of therapy treatment. The statistics globally in cancer is a challenge to the healthcare sector in any country. It has been found that in 2012 approximately 14 million new cases of cancer occurred globally, and these data do not include the patients with skin cancer and other types of malignant melanoma. It caused about 8.2 million deaths or 14.6% of the entire mortality rate globally.

The most common cancer types in males are lung cancer, prostate cancer, colorectal cancer and stomach cancer. The most frequent events in woman are breast cancer, colorectal cancer, lung cancer and cervical cancer. However, if one would include skin and all types of malignant melanoma, this would account for about 40% of the cases. With respect to children, the cancer types vary, and the most common are acute lymphoblastic leukemia and brain tumors. In Africa however, the most common cancer disease is Non-Hodgkin's lymphoma. The financial costs of cancer have been estimated at $1.16 trillion US dollars per year as of 2010.

Personalized medicine is a medical treatment model, tailored to the individual patient. Within Personalized Medicine optimal therapies are often employed for selecting appropriate treatments based on the context of a patient's genetic content or other molecular or cellular analysis The use of genetic information, pharmacogenomics, has played a major role in certain aspects of personalized medicine, and the term was first coined in the context of genetics, though it has since broadened to encompass all sorts of targeted personal read out diagnosis testing.

Some of the modern advances in personalized medicine rely on "OMICS" technologies (biology research field ending in -omics, such as genomics, proteomics or metabolomics) that confirms a patient's fundamental biology, by the mapping of DNA/RNA, and/or protein which initially leads to confirming disease. The concept of 4P medicine utilizes these OMICS platforms, and today plays a mandatory role in modern healthcare where the Obama healthcare system is investing significant resources for its developments.

By supportive biomolecular analysis, in order to confirm a given disease mutation and whether it can be linked to a certain disease, researchers often do a study called a GWAS, a genome wide analysis. A GWAS study will look at one disease, and then sequence the genome of many patients with that particular disease to look for shared mutations in the genome.

Specific somatic or point-mutations that are determined to be related to a disease by the GWAS analysis can then be used to diagnose specific disease genotypes and possibly phenotypes, by looking at their genome sequence to find that same mutation.

Multiple genes collectively influence the likelihood of developing many common and complex diseases. Consequently, the advances in personalized medicine will create a significant diversification of treatment approaches that has been proven to be specific to the individual and their genome signatures. Personalized medicine will improve efficacy, by providing better diagnose developments, resulting in earlier intervention, and more efficient drug development and therapies.

By being able to investigate each and every patient on an individual basis will allow for a more accurate diagnosis and personalized treatment plan. Modern genotyping provides a detailed account of an individual's DNA sequence; their genome can then be compared to a reference genome, in order to assess the existing genetic variations that can account for conceivable disease status.

In addition to the precise treatment, personalized medicine is able to greatly aid in the advancements of preventive care. This has been proven over the years, where women are being genotyped for certain mutations in the BRCA1 and BRCA2 genes, respectively, investigating predisposition because of a family history of breast-, or ovarian cancer.

By the identity of a multitude of sources of disease presentation, which are mapped out according to mutations that exist within a genome, indicate that the easier they can be identified in an individual, the better opportunity for successful treatments.

By having the genetic content of an individual, will ultimately allow better guided decisions in determining the source of the disease and thus treating it or preventing its progression.

Companion diagnostics is the definition that is being used to test efficacy and safety of a drug specific to a targeted patient group or sub-group. In many instances the companion diagnostics assay is helpful in enhancing the therapeutic treatment efficiency.

Today, in modern healthcare, it is common that physicians often use a trial and error strategy until they find the treatment therapy that is most effective for their patient.

With personalized medicine, these treatments can be more specifically tailored to an individual and give insight into how their body will respond to the drug and if that drug will work based on their genome, and subsequent transcript with a final expressed protein.

Lately, the cancer field has discovered a great deal about the genetic variety of cancer types that is presented within traditional disease pathology. The definition of the tumor heterogeneity among cancer patients is a genetic diversity within a single tumor. Among other prospects, these discoveries raise the possibility of identifying, that drugs with poor outcome applied to a general population, may yet be successful for a proportion of cases with a particular genetic profile.

In Ho Jeong Kwon et. al. (Arch. Pharm. Res. (2015) 38:1718-1727), it was shown that MALDI mass spectrometry imaging (MSI) provides a technology platform that allows the accurate visualization of unlabeled small molecules within the two-dimensional spaces of tissue samples. Mass spectrometry imaging data within various cancers such as malignant melanoma in patients administered with vemurafenib, a protein kinase inhibitor that is targeting BRAF mutated proteins is also provided.

Hence, improved treatment methods taking the individual into account, would be advantageous with novel methods that could aid in the guidance of treatment in the highly complex disease biology.

SUMMARY OF THE INVENTION

Accordingly, the present invention preferably seeks to mitigate, alleviate or eliminate one or more of the above-identified deficiencies in the art by providing a method of determining the specific binding of a ligand reversibly binding to a binding site in a tissue sample using displacement competitive inhibition. The method comprising incubating the ligand in the absence of a labeled ligand on a first tissue specimen, incubating the ligand in the presence of a labeled ligand on a second tissue specimen, the first and the second tissue specimens being adjacent sections of specimen. MALDI imaging mass spectrometry is used to subsequently visualizing bound ligand localization, using in the first and second tissue specimen, respectively.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 7 shows (B) an image capture from a tissue section of a cancer patient where 100 nM Vemurafenib was administered within the tissue with corresponding histology image (A), and then followed by (C) experiments where 100 mM $^{13}$C-vemurafenib (m/z 389.1) and 100 nM Vemurafenib (m/z 383.1) was administered within the tissue, looking at the remains of Vemurafenib (m/z 383.1) after 100 mM $^{13}$C-vemurafenib competitive binding, and with the corresponding histology image (D);

FIG. 8 (A) shows an image capture with Vemurafenib (MS/MS) signal response (m/z 383.1) from a tissue section from a patient lacking the V600E mutation in the BRAF target protein (negative control) where 100 nM Vemurafenib was administered, (B) shows an image capture with Vemurafenib (MS/MS) signal response (m/z 383.1) from the tissue section where 100 nM Vemurafenib was administered within the tissue from a patient with a V600E mutation in BRAF target protein, and (C) shows an image capture with $^{13}$C-Vemurafenib (MS/MS) signal response (m/z 389.1) from a tissue section where 100 nM Vemurafenib and 1 µM $^{13}$C-Vemurafenib was administered within the tissue;

FIG. 9 (A) shows an image capture with Vemurafenib (MS/MS) signal response (m/z 383.1) from a tissue section where Vemurafenib (100 nM) was administered within the tissue from a patient with a V600E BRAF mutation in BRAF target protein, (B) shows an image capture with Vemurafenib (MS/MS) signal response (m/z 383.1) from a tissue section where Vemurafenib was administered within the tissue from a patient lacking the V600E BRAF mutation in the BRAF target protein (negative control), and (C) shows an image capture with $^{13}$C-Vemurafenib (MS/MS) signal response (m/z 389.1) from a cell of the tissue section where 100 nM Vemurafenib and 1 µM $^{13}$C-Vemurafenib was administered in a patient with a V600E BRAF mutation in BRAF target protein; and FIGS. 10 (A) to (D), show an image capture for a co-incubation titration experiment, where a fixed concentration of Vemurafenib is administered to the tissue samples and $^{13}$C-Vemurafenib is added in a titration series of increasing concentration from (A) to (D) respectively, 100 nM, 10 µM, 100 µM and after incubation the $^{13}$C-Vemurafenib (MS/MS) signal response (m/z 389.1) is measured.

DESCRIPTION OF EMBODIMENTS

Figure 1A:
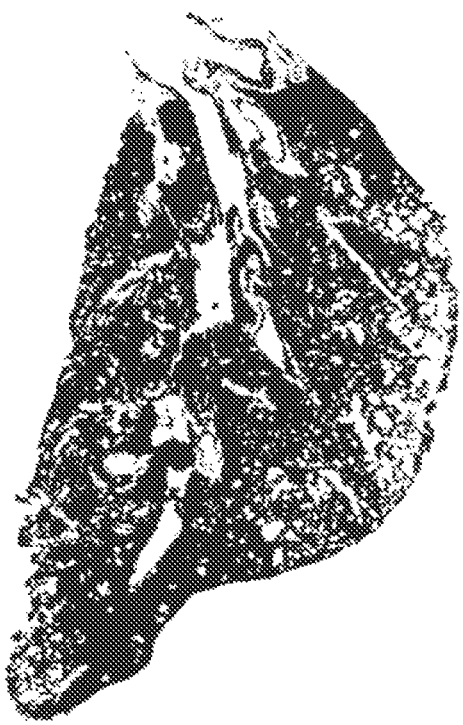
FIG. 1 is an illustration of a MSI experimental procedure showing (A) histologically stained (H&E) tissue section, (B) a tissue section impregnated with matrix (MS matrix), (C) an ion signal from a drug from an MS experiment and (D) an overlay of the histological section and the ion signals.

The following description focuses on embodiments of the present invention applicable to a mass spectrometry method for measuring drug specificity and drug selectivity in a tissue sample, and in particular to a multimodal assay capable of screening for the presence of a single or multiple drug(s) and metabolite(s) in patient samples by mass spectrometry imaging, and a method for characterizing the drug interaction properties with the patient tissue sample. However, it will be appreciated that the invention is not limited to this application but may be applied to other applications of measuring molecule properties and interactions in tissue samples.

Mass spectrometry (MS) is a valuable analytical technique because it measures an intrinsic property of any given molecule, its mass, with very high sensitivity. MS can therefore be used to measure a wide range of molecule types and a wide range of sample types/biological materials. In this ionization process, the precursor ion is activated by acceleration into a mass-selective linear ion trap under conditions whereby some of the fragment ions formed are unstable within the trap. After a time delay the stability parameters of the ion trap are changed to allow capture of fragments that were previously unstable. The result is a product ion spectrum that originates from precursor ions with a modified internal energy distribution. It is possible to follow the evolution of the precursor internal energy distribution for many milliseconds after admittance of the precursor ions into the linear ion trap. Time-delayed fragmentation product ion spectra typically display reduced sequential fragmentation products leading to spectra that are more easily interpreted. Several important experimental parameters important to time-delayed fragmentation have been identified and the technique has applications for both small precursor ions and multiply charged molecules.

Tandem mass spectrometry (MS/MS) is at the heart of most of modern mass spectrometric investigations of complex mixtures. The fragmentation involves activation of a precursor ion via collisions with a target gas and may produce charged and neutral fragments. The nature of the fragment ions, as well as their intensities, is often indicative of the structure of the precursor ion and thus can yield useful information for the identification of unknown analytes, as well as providing a useful screening technique for different classes of analytes. Activation via multiple collisions both prolongs the activation time and enables higher energies to be deposited into precursor ions. Higher collision gas pressures also imply higher collision relaxation rates.

Matrix-assisted laser desorption/ionization (MALDI) is a soft ionization technique used in mass spectrometry. Traditional MALDI is a three-step process, where the sample is mixed with a suitable matrix material and applied to a sample metal plate. A pulsed laser irradiates the sample, and the analyte molecules are ionized by being protonated or deprotonated in the hot plume of ablated gases, and can then be accelerated into the mass spectrometer for analysis.

MALDI mass spectrometry imaging is defined as the use of matrix assisted laser desorption with a mass spectrometry imaging technology (MALDI-MSI), where the sample, consisting of a thin tissue section. The preparation of the tissue section samples are a vital step within MSI. MALDI matrix is added to the thin tissue slices mounted on conductive microscope slides. The matrix substance must absorb at the laser wavelength and ionize the analyte. Matrix selection and solvent system relies heavily upon the analyte class desired in imaging. The analyte must be soluble in the solvent in order to mix and recrystallize the matrix. The matrix must have a homogenous coating in order to increase sensitivity, intensity, and shot-to-shot reproducibility. Minimal solvent is used when applying the matrix in order to avoid delocalization.

Following this step, the microscope slide is inserted into a MALDI mass spectrometer. The instrument will record the spatial distribution of molecular species such as drug compounds, and metabolite drug molecules. Thereafter, suitable image processing software can be used to import data from the mass spectrometer to allow visualization and comparison with the optical image of the sample.

The tissue sections can also undergo histological staining after the MSI investigation is completed. This is performed in order to target areas of interest, and pretreated with washing in order to remove species that suppress molecules of interest.

Figure 1B:
Figures 1C, 1D:
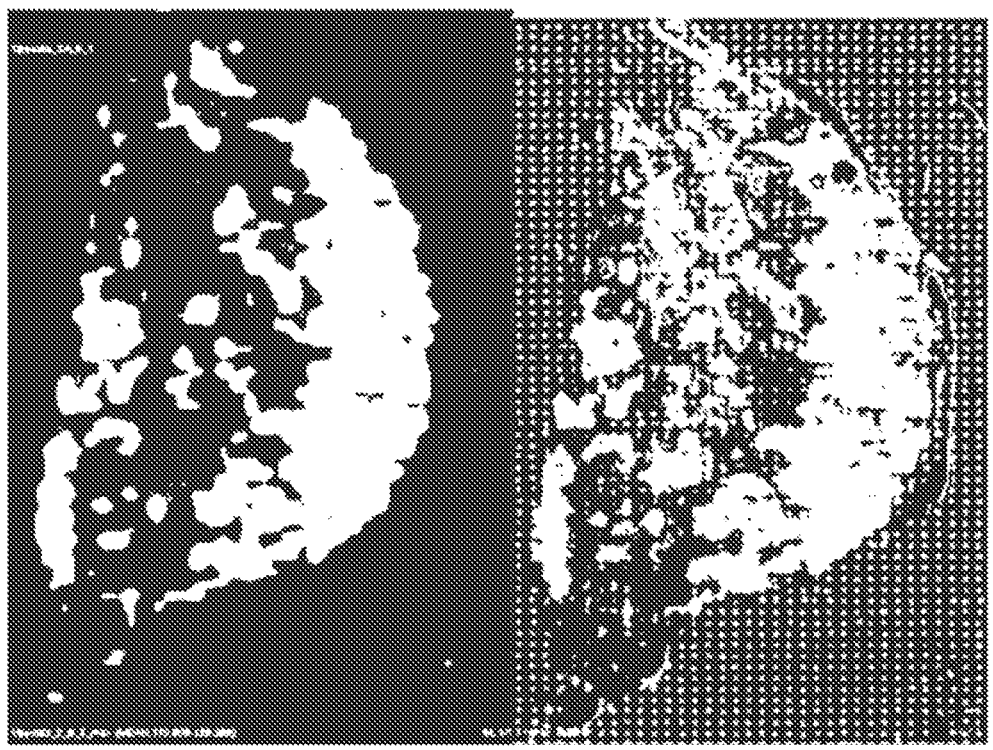

FIG. 1 illustrates a MSI experimental procedure. The tissue is characterized by histological staining. The MSI experiments are made by matrix deposition, followed by MSI experiments, conducted by providing drug analysis. The histological section image and the ion signals can be overplayed and presented in the far right image capture by overlaying the two images and identifying common co-localizations. The overlay provides evidence of the tumor cell localization within the tissue and the co-localization of the drug. Images are constructed by plotting ion intensity versus relative position of the data from the sample, where the spatial resolution highly impacts the molecular information gained from analysis.

The application of this technique to biological studies has increased significantly since its introduction. MALDI-MSI is providing major contributions to the understanding of diseases, improving diagnostics, and drug delivery. MALDI-MSI has been able to differentiate between drugs and metabolites and provide histological information in cancer research, which makes it a promising tool for finding new protein biomarkers. The mass spectrometry imaging (MSI) technology is currently utilized in the drug discovery as well as the drug development process within the pharmaceutical industry.

With regard to drug characterization, the MSI technology has been utilized in industry to investigate drug distribution in the main organs. ADME pharmacokinetic properties along with possible drug toxicity and drug metabolism, are key regulatory considerations that the FDA and EMEA agencies demands in order to approve new drug entities, where animal models are commonly used. Nowadays, the MALDI platform is the most common mass spectrometry technology applied within pharma-, and biotech industry as well as national research centers and academia.

Micro-heterogeneities within the tissue can be compensated for by using a matrix internal standard that is then used for data and quantitation normalization. The overall tissue coverage of the matrix (with or without) the internal standard by a uniform thin layer of matrix crystals on the tissue surface is of mandatory importance in order to provide reproducible and high quality data.

Figure 2:
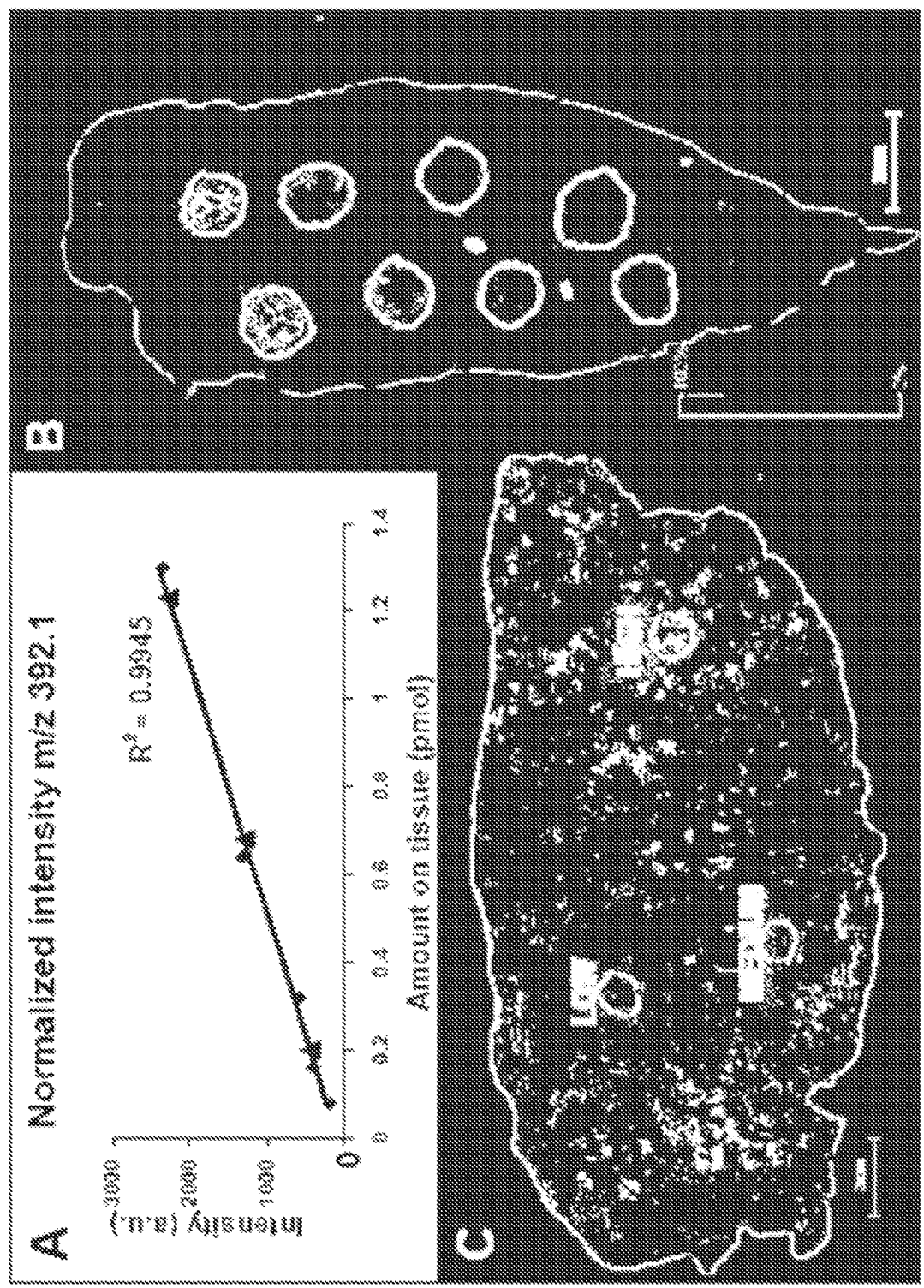
FIG. 2 is an Illustration of the drug quantitation principle of the method and the (A) linear relationship in-between (B and C) drug concentration and signal response by mass spectrometry imaging.

Quantitation of drugs can be made by MALDI/MSI and have been developed over the years and an example is illustrated in FIG. 2 (C). Drug quantitation can be achieved by applying known concentration of drug solution preparations and apply this onto the tissue surface (B). Varying levels of the drug solutions are next analyzed by MALDI imaging experiments. The resulting signal response intensities can be plotted against drug concentrations and a linear relationship can be established within a calibration experiment (A), as shown in FIG. 2.

Figure 3A:
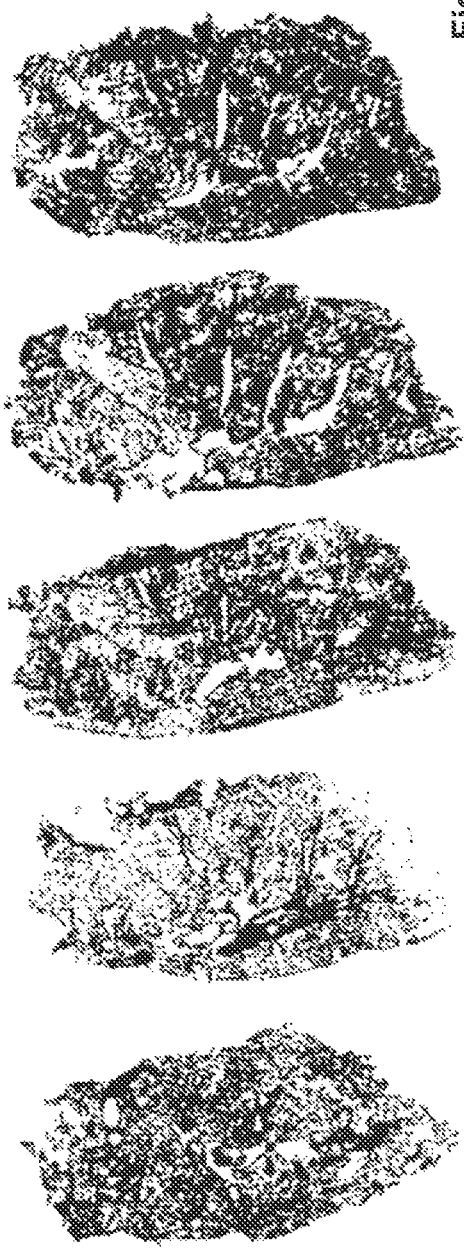
FIG. 3 shows (A) images of histological sections with a 10 micrometer spacing in-between the respective tissue section throughout the tumor tissue, and (B) Mass Spec Tissue Imaging of Drug Compound and its specific localization.
Figure 3B:
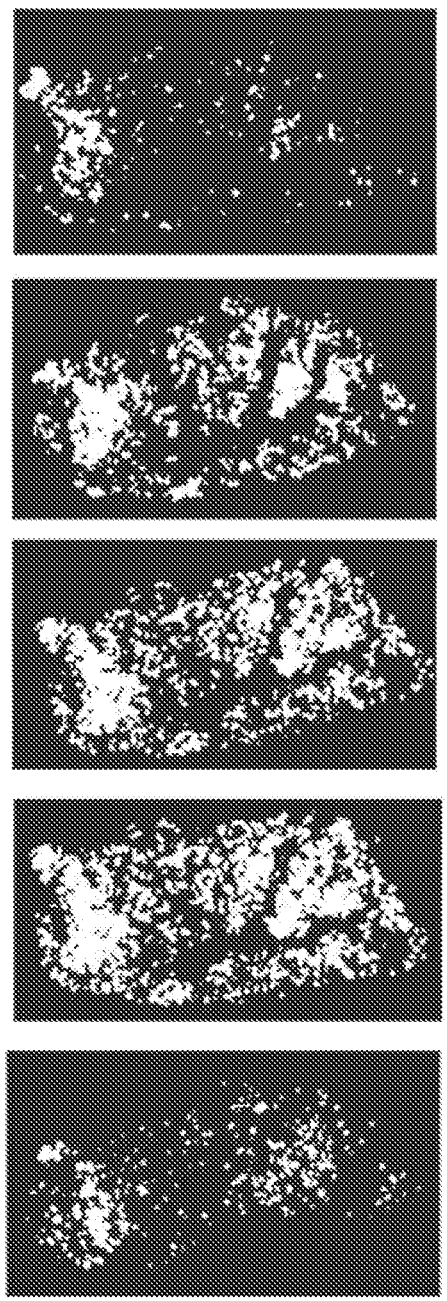

MALDI/MSI is label-free and can be applied to native drug structures and their metabolites within any tissue environment. As the drug diffusion occurs through the organ, a concentration gradient will occur through the various cell layers. This drug and metabolite(s) disposition localized in-between cells or within cells throughout the tissue will be dependent on the microenvironment of the tissue as well as on the pharmaco-kinetic variables for a given drug structure. An identified spatial distribution of drug in concentration gradients throughout the tissue structure and morphology is shown in FIG. 3A-B that makes it possible to align the drug levels and correlate that to the tissue morphology. In FIG. 3, histological images of the tissue (FIG. 3A), here sorted in adjacent sections, describing the structure and morphology of the tumor. The tumor environment is used as the architecture for the drug image data (MSI experiments, illustrated in FIG. 3B), analyzing Vemurafenib (MS m/z 490.078). As can be seen, different tissue structure elements are co-localized with the Vemurafenib signal.

Many different MS-based quantitative methods have been in development over the last decade, which rely on a small number of fundamental techniques, usually involving some kind of standard against which to compare.

Relative quantitative drug imaging methods measure the relative abundance ratio between two or more samples and can be divided into label-based and label-free methods. Different techniques offer different advantages; for example, in vivo labeling is more efficient, labeling potentially every molecule in a cell, although it is often impractical for some samples (e.g. human tissue) whereas in vitro methods can be applied for any type of sample in principle. In all cases, there are common challenges for calculating quantitative values at the drug molecule level.

MS-based imaging quantitative methods can be classified into two groups in either absolute quantitation, and/or relative quantitation.

The label free drug molecule can be quantified by relative analysis methods that relate one signal response to another with the respective signal read-out signals. Peak intensities are determined and ratios calculated for molecular matched in different experiments.

Absolute quantification has proved a challenge, and strategies often involve the use of a labeled version of the drug molecule. Drug compounds can usually be distinguished by incorporating stable isotopes within the structure, thereby altering the mass of all other molecules in any given sample in a predictable fashion (as shown in FIG. 4). These stable isotopes may be incorporated metabolically into (ideally) all drug compound molecules, in vivo, or a chemical reagent can be used to label in vitro. The isotope labeled drug have exactly the same physico-chemical properties as the un-labeled drug.

There are currently few therapeutic options for patients with cancer diseases, and new insights into the pathogenesis of this lethal disease are urgently needed. Studies with patients in feasibility studies in combination with disease models in rodents has been the strategy our research teams have been taking for a number of years. Further, the correlation in-between a given rodent model with administered drug on one hand and the ability to utilize controlled administrations to tissue sections from organs isolated with the intact tumor environment is a valuable tool for drug characterizations in a disease model.

Figure 4A:
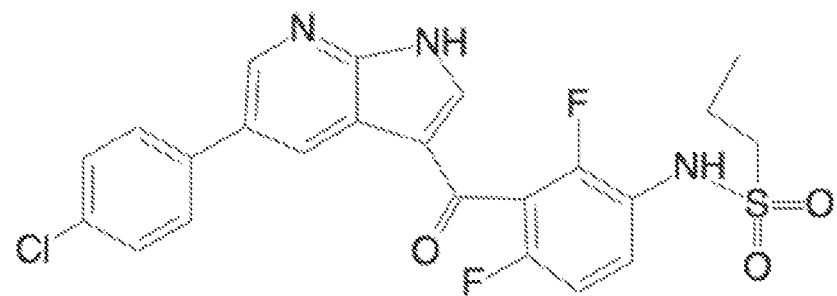
FIG. 4 illustrates (A) the molecular structure of the drug Vemurafenib and (B) molecular structure of the isotope labeled $^{13}$C-Vemurafenib, wherein the asterisk marks the carbon-13 isotopes.

In the study underlying the present invention, Vemurafenib, a BRAF enzyme inhibitor for the treatment of late-stage melanoma, is used to study drug-tumor interaction. Vemurafenib has been shown to cause programmed cell death in melanoma cell lines by interrupting the B-Raf/MEK step on the B-Raf/MEK/ERK pathway. FIG. 4A shows the molecular structure of the drug Vemurafenib (wherein the asterisk represents the $^{13}C$ isotopes. Except for the incorporation of carbon-13 isotopes in the labeled $^{13}C$-Vemurafenib, the structures are identical. Of interest is that Vemurafenib is only effective if BRAF has the common V600E mutation or the rarer type BRAF V600K mutation. About 60% of melanomas have these mutations, but melanoma cells without these mutations are not inhibited by Vemurafenib.

Figure 6:
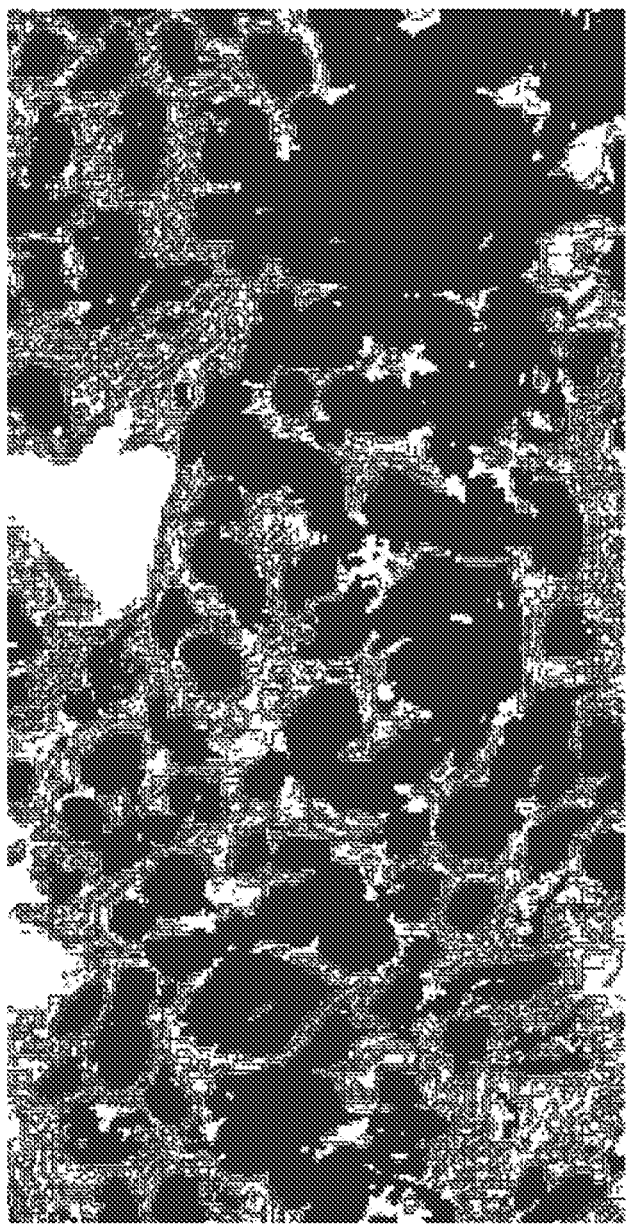
FIG. 6 shows an image capture from a tissue section of a cancer patient where the single cell disposition morphology is shown.

FIG. 5 shows MSI images generated from a melanoma cancer tumor where Vemurafenib signal response is shown in MS-mode, top right shows the fragment ion generated from parent ion (MS/MS), lower left shows second fragment ion from Vemurafenib compound signal (MS/MS), and lower right shows the overlay of all three signals. Applications that are performed at single cell resolution are preferable as the localization of the drug and metabolite(s) can be made with higher precision and accuracy. FIG. 6 shows a histology image where single cell disposition is shown in a tissue section. Laser desorption mass spectrometry (MALDI) is being used to identify the drug (Vemurafenib) localization in the cancer tissue of a patient. The laser diameter captures images at a resolving power of 30 micrometers in spatial resolution within the tissue compartments.

One limitation for traditional MALDI-MSI drug localization is that drug and drug metabolites may non-specifically bind or stick to non-relevant parts of a tissue sample. This becomes especially evident for non-optimized drugs with lower solubility or requiring higher doses. To minimize this, samples are washed after drug incubation, here with PBS 3 times and then followed by washing with MilliQ water 3 consecutive times. However, while such washing to some extent will reduce MS-signals resulting from unspecific binding, it still pose a problem, especially given the authorities, such as FDA and EMEA, requiring detailed information regarding drug distribution in the main organs in approving new drug entities (NCEs).

In the method of the invention, the ligand, such a small molecule drug, bound in the tissue sample is displaced by a labeled ligand with a higher concentration by competitive inhibition. Practically, a tissue sample from a patient is incubated with unlabeled ligand, without and with an isotope-labeled ligand on adjacent sections of tissue specimens and then visualizing the locations and quantifying bound ligand and/or labeled ligand using MALDI imaging mass spectrometry. Whereas unspecific binding not is competitive, specific binding is. The use of an isotope-labeled ligand therefore allows for distinguishing between specific and unspecific binding.

In one embodiment, a method of determining the specific binding of a ligand reversibly binding to a binding site in a tissue sample uses displacement competitive inhibition. The method comprises incubating the ligand (unlabeled) in the absence of a labeled ligand on a first tissue specimen, incubating the ligand (unlabeled) in the presence of a labeled ligand on a second tissue specimen, the first and the second tissue specimens being adjacent sections of specimen. Subsequently, ligand localisation is visualizing using MALDI imaging mass spectrometry in the first and second tissue specimen, respectively.

In one embodiment, the ligand and labeled ligand are homologs, specifically binding to the same binding site. In one embodiment, the labeled ligand is an isotope-labeled, such as a deuterium labeled ligand or a $^{13}C$-isotope labeled ligand. In one embodiment, the ligand is Vemurafenib and the labeled ligand is $^{13}C$-Vemurafenib. In on embodiment, the ligand and/or labeled ligand are quantified using MALDI imaging mass spectrometry.

In detail, we performed the experimental steps consecutively;
(1) Making 10 micrometer sectioning of the frozen Human Malignant Melanoma tissues performed at −20° C. Thereafter, (2) sample preparation was preformed by slowly thawing and drying the tumor sections at room temperature. Then, the sections were immersed into methanol for 5 min and dried at room temperature. Correspondingly, frozen Human healthy tissue resected from lymphoid nodes were handled in the same way, and used as negative controls. (3) Drug incubation was performed for one hour by using unlabeled ligand, here Vemurafenib, at a concentration of 100 nM (nanomolar) to determine the binding of the ligand molecule to its protein target. Co-incubation experiments were also performed with patient tumor sections with a ligand, here Vemurafenib, concentration of 100 nM and an excess of stable isotope labeled ligand, here $^{13}C$-Vemurafenib. During titration experiments, the concentration of stable isotope labeled Vemurafenib was 100 nM, 1 µM, 10 µM and 100 µM, (micro Molar), respectively. (4) After incubation, the sections were washed by PBS 3 times and then followed by washing with MilliQ water 3 consecutive times, and (5) mass spectra were obtained using a MALDI LTQ-Orbitrap XL instrument (Thermo Scientific, Germany), and compound signals were obtained by the orbitrap and ion trap. Image analysis was conducted using ImageQuest (Thermo Scientific, Germany). For histological analysis, both H&E staining and immuno-histochemical analysis using monoclonal antibody against BRAF V600E were conducted.

In an embodiment, sectioning of frozen tissue is performed and a first and second tissue specimen is prepared from adjacent sections of the frozen tissue. In one embodiment, said sections are thawed, dried and immersed into methanol for 5 min. In one embodiment, ligand (i.e. drug) incubation is performed for one hour using unlabeled ligand, and co-incubation is performed for one hour using unlabeled ligand and an excess of labeled ligand. In one embodiment, sections are washed, preferably with PBS 3 times and then followed by washing with MilliQ water 3 consecutive times. In one embodiment, mass spectra are obtained using a MALDI LTQ-Orbitrap instrument, signals are obtained by the orbitrap and ion trap and image analysis is conducted using ImageQuest. In one embodiment, histological analysis is obtained by H&E staining and/or immuno-histochemical analysis using monoclonal antibody.

In one embodiment, ligand binding to the protein target location is confirmed by co-localization, such as by immuno-histochemical analysis using monoclonal antibody specific for the protein target.

The impact of this is shown in FIG. 7, an image capture from a tissue section of a cancer patient, where (A) shows the histology image of the tissue sample and (B) shows an MSI image of the same tissue sample after 100 nM Vemurafenib was administered within the tissue, where Vemurafenib signal response is shown in MS-mode. This is followed by a tissue section of the cancer patient, where (D) shows the histology image of the tissue sample and (C) shows MSI image of the tissue sample where 100 mM $^{13}C$-Vemurafenib and 100 nM Vemurafenib was administered within the tissue, where the Vemurafenib signal response is shown in MS-mode. Depending on the assay format chosen, the Vemurafenib and $^{13}C$-Vemurafenib may be added simultaneously, thereby providing a method readout that is kinetically competitive upon binding to the target protein, or separately. As clearly shown, the Vemurafenib signal in FIG. 7 (A) is extinguished after the competitive inhibition of the $^{13}C$-Vemurafenib. Due to the thousand fold higher concentration of $^{13}C$-Vemurafenib, bound Vemurafenib will be virtually out-competed by the $^{13}C$-Vemurafenib. For unbound Vemurafenib non-specifically sticking to parts of the tissue sample, it will not be specifically out-competed by the $^{13}C$-Vemurafenib. Thus, specifically bound Vemurafenib can be determined using displacement competitive inhibition. Preferably, the labeled ligand is formulated at a higher concentration than then unlabeled ligand during the displacement, such as five to ten thousand fold higher concentrations of the labeled ligand compared to the unlabeled ligand. Normally, the preferred concentration of the unlabeled drug is in the nanomolar range and the concentration of the isotope labeled drug is in the micromolar range.

In one embodiment, the concentration of labeled ligand is higher, such as 5 to 10 000-fold higher, or such as 10 to 1000 fold higher, than the concentration of the unlabeled ligand during displacement competitive inhibition. In one embodiment, the unlabeled ligand is of nanomolar concentration and the isotope labeled ligand is of micromolar concentration.

In FIGS. 8 and 9, the addition of isotope labeled compound (i-Vemurafenib) shows a competitive exchange of Vemurafenib to i-Vemurafenib, a substitution that provides evidence of specific and selective drug binding.

In FIG. 8, tissue sections are shown from (A) a negative control from a patient lacking the V600E BRAF mutation in the BRAF target protein and, (B) and (C), tissue sections from a patient with a V600E mutation in BRAF. In (A) to (C), 100 nM Vemurafenib was administered within the tissue and image is captured with Vemurafenib (MS/MS) signal response (m/z 383.1). In (C), 1 µM $^{13}$C-Vemurafenib was co-administered within the tissue and image is capture with $^{13}$C-Vemurafenib (MS/MS) signal response (m/z 389.1), outcompeting the 100 nM Vemurafenib.

In FIGS. 9 (A) and (C), tissue sections are shown from a patient with a V600E mutation in BRAF, and in (B) a negative control from a patient lacking the V600E BRAF mutation in the BRAF target protein. In (A) to (C), 100 nM Vemurafenib was administered within the tissue and image is captured with Vemurafenib (MS/MS) signal response (m/z 383.1). In (C), 1 µM $^{13}$C-Vemurafenib was co-administered within the tissue and image is capture with $^{13}$C-Vemurafenib (MS/MS) signal response (m/z 389.1), outcompeting the 100 nM Vemurafenib.

The control tissues confirm that Vemurafenib does not bind to a large extent in tissue lacking the V600E BRAF mutation. Instead, the tissue samples from patients with a V600E mutation in BRAF shows clear binding to cells localized within the tissue. Furthermore, the clear cut specificity of competitive binding proves the specificity of the drug binding to the cancer cells and protein target.

With the current method, data generated provides specific binding properties, which can be determined after Vemurafenib and/or after i-Vemurafenib drug administration. In FIGS. 10 (A) to (D), a Co-incubation titration experiment is shown. The isotope labeled compound ($^{13}$C-Vemurafenib) additions shows a competitive exchange of Vemurafenib to i-Vemurafenib, a substitution that provides evidence of specific and selective drug binding.

In an embodiment, the method comprises incubating unlabeled ligand with at least two different concentrations of labeled ligand on adjacent sections of tissue specimens. In one embodiment, the method comprises using a titration of different labeled ligand concentrations.

The i-Vemurafenib (here $^{13}$C-Vemurafenib) Isotope Signal from FIG. 10 is summarized in table 1 below. It clearly shows that the competitive binding of i-Vemurafenib is increasing with increasing levels of administration. The mass spectrometry results clearly indicate the linear relationship in-between the i-Vemurafenib drug concentration and the binding to the cancer cells, with a background of Vemurafenib. Furthermore, drug kinetics as well as the metabolite kinetics upon treatment can be determined using the methodology described. By plotting the titration results in a dose response curve, the IC50 value, the concentration required for 50% inhibition of the Vemurafenib by the $^{13}$C-Vemurafenib, can be derived. Similarly, other constants such as the ligand dissociation constant ($K_d$) can be derived from the IC50 value, for example using the Cheng and Prussoff relationship. For an inhibitor (such as Vemurafenib, which acts as an inhibitor in the B-Raf/MEK step on the MAPK/ERK pathway), the inhibition constant ($K_i$) can be derived. Depending on the target protein characteristics as well as the mode of inhibition (i.e. competitive, uncompetitive or mixed inhibition), the suitable equation is used for calculating inhibition constant ($K_i$). Commonly, $K_i$ and IC50, measured under the same assay conditions, of same inhibitor or two different inhibitors ($I_1$ and $I_2$) with the same mechanism of action can be compared as: $K_{i,1}/K_{i,2}=IC_{50,1}/IC_{50,2}$.

Thus in one embodiment, the method is used calculate kinetic binding characteristics for the ligand and/or metabolite and/or target receptor. In one embodiment, the kinetic binding characteristics are $K_d$ (dissociation constant), $K_i$ (inhibitor dissociation constant), IC50 (half maximal inhibitory concentration).

The binding properties are important in order to elucidate and understand the mode-of-drug-action. The drug mechanisms are key in the treatment of cancer patients, and are directly related to the possible toxicity aspect, and safety of the patient. Hence, the method of the invention may provide detailed drug-tissue interaction information for an individual patient. For instance if a drug binds specifically to the tumor type, and if the drug binds homogeneously to all tumor tissue, thus enabling improved treatment methods taking the individual into account, aiding in the guidance of treatment in the highly complex disease biology.

The binding properties can also be probed using a mixture of more than one drug compound (i.e. ligand) and isotope compound (i.e. labeled ligand) in a pair. This drug cocktail mixture provides unique image captures where the binding properties of single, or multiple drug binding occurs over a given time course. The kinetics of specific binding properties is thereby determined by drug binding specificity information and detailed data.

In one embodiment, the method uses a mixture of more than one pair of ligand and labeled ligand, that is, at least one first ligand and corresponding first labeled ligand, and a second ligand, and corresponding second labeled ligand, to determining the specific binding of a first ligand and/or a second ligand reversibly binding to a binding site in a sample using displacement competitive inhibition.

The drug (i.e. ligand) cocktail mixture may also include multiple drugs binding to multiple binding targets. For such mixtures, it may be of high importance to determine that all cocktail constituents bind selectively to the tumor tissue, to help select an effective drug cocktail, or for the case where a treatment using a specific drug cocktail has proven clinically effective but having extensive side effects, to optimize a drug cocktail for treatment In one embodiment, the method uses a mixture of more than one pair of ligand and labeled ligand, that is, at least one first ligand and corresponding first labeled ligand, binding to a first target, and a second ligand, and corresponding second labeled ligand, binding to a second target. Displacement competitive inhibition is used to determine the specific binding of the first ligand and/or a second ligand.

The labeled ligand may be added to a system where the ligand-receptor binding is already at, or close to, equilibrium after incubation. This way, the competitive exchange may be monitored during a time course, providing both information about the dispersal of the drug in the tissue and possibly non-equilibrium kinetic data. In one embodiment, the method the method comprises (1) incubating a tissue sample with unlabeled ligand, and thereafter (2) incubating said tissue sample with labeled ligand. That is, the ligand may be added to the tissue sample first (at one time point) and the labelled ligand is added at a later time (at a second time point). Such experiments may provide more information with regards to the drug penetration and distribution in the sample, and possibly further kinetics information, such as residence time ($t_r$) and half-life ($t_{1/2}$) of a bound ligand, characteristics that are not concentration dependent and often important for drug efficacy.

Materials and Methods

The following examples are mere examples and should by no mean be interpreted to limit the scope of the invention. Rather, the invention is limited only by the accompanying claims.

The frozen Human Malignant Melanoma tissues were resected from lymphoid nodes, constituting the tumor tissue. The tissue sections were sections with 10 µm (micro meter) slices thick by the use of a cryostat, performed at −20° C. After sectioning, the slices were slowly thawed and dried at room temperature. Then, the sections were immersed into methanol for 5 min and dried at room temperature. Correspondingly, frozen Human healthy tissue resected from lymphoid nodes was used as negative controls.

Incubation was made for one hour by using unlabeled Vemurafenib at a concentration of 100 nM (nanomolar) to determine the binding of the drug molecule to its protein target. Co-incubation experiments were also performed with patient tumor sections with a Vemurafenib concentration of 100 nM and an excess of stable isotope labeled Vemurafenib. The incubation time during competitive binding was 1 hour. The incubation time can be varied depending on the type of experiment performed. During titration experiments, the concentration of stable isotope labeled Vemurafenib was 100 nM, 1 µM, 10 µM and 100 µM, (micro Molar), respectively.

Figure 4B:
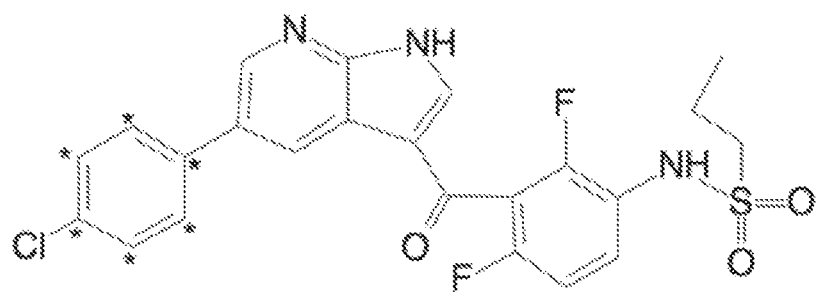
Figure 5A:
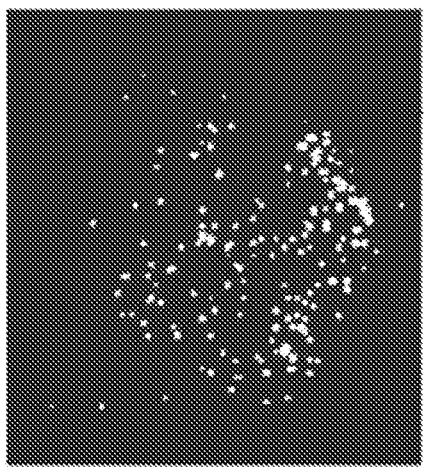
FIG. 5 shows MSI images generated from a melanoma cancer tumor where (A) Vemurafenib signal response is shown in MS-mode (m/z 490.078), (B) shows the fragment ion generated from parent ion (MS/MS, (m/z 383.1)), (C) shows second fragment ion from Vemurafenib compound signal (MS/MS, (m/z 262.1)), and (D) shows the overlay of all three signals.
Figure 5B:
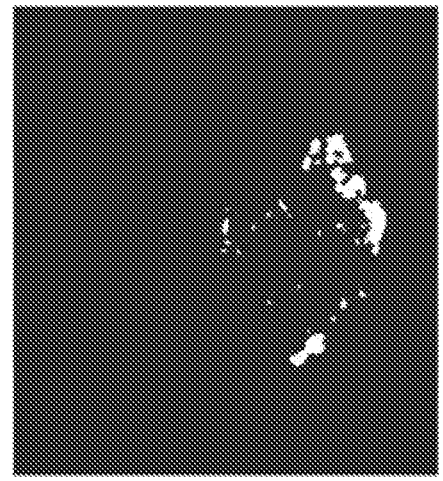
Figure 5C:
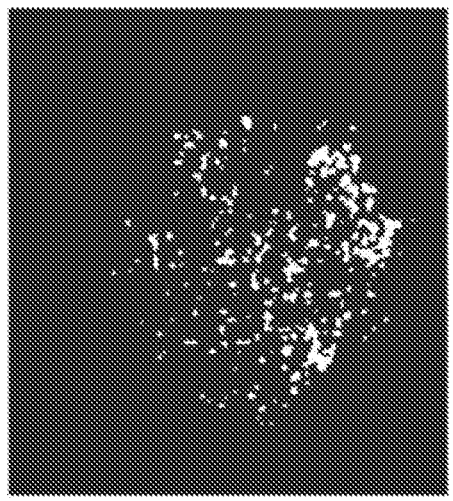
Figure 5D:
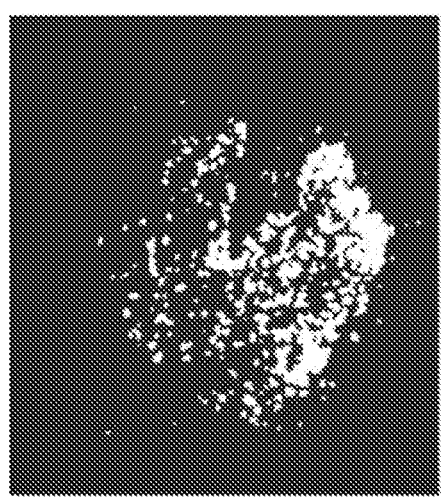

The structural formulas of Vemurafenib and the isotope labeled $^{13}$C-Vemurafenib are shown in FIGS. 4A and 4B.

After incubation, the sections were washed by PBS 3 times and then followed by washing with MilliQ water 3 consecutive times.

The mass spectra were obtained using a MALDI LTQ-Orbitrap XL instrument (Thermo Scientific, Germany). The compound signals were obtained by the orbitrap and ion trap. Image analysis was conducted using ImageQuest (Thermo Scientific, Germany). For histological analysis, both H&E staining and immuno-histochemical analysis using monoclonal antibody against BRAF V600E were conducted.

Binding intensity was calculated by identifying the area of biding from the mass spec image and the intensity read is calculated by the ImageQuest software of the instrument from the signal and background data.

Results

In FIG. 6, an image of a human Malignant Melanoma tissue section treated for MSI experiments shows the single cell disposition morphology of the tissue section samples. Laser desorption mass spectrometry used to identify the drug (Vemurafenib) localization in the cancer tissue, has a laser diameter which captures images at a resolving power of 30 micrometers in spatial resolution within the tissue compartments.

FIG. 5 (A) shows a MSI image of Vemurafenib signal response in MS-mode of a human Malignant Melanoma tissue section incubated unlabeled Vemurafenib. The signal response of the first and second fragment ions generated from parent ion (MS/MS) of Vemurafenib is shown in FIGS. 5 (B) and (C) respectively. An overlay of all signals (A-C) is shown in FIG. 5 (D).

Co-incubation experiments are shown in FIG. 7. FIG. 7 (A) shows a histology image of a human Malignant Melanoma tissue section of a patient, and (B) an image capture from the tissue section where 100 nM Vemurafenib was administered within the tissue. FIG. 7 (D) shows histology image of another human Malignant Melanoma tissue section, and (C) Co-incubation experiments where 100 mM $^{13}$C-Vemurafenib and 100 nM Vemurafenib was administered within the tissue. The addition of isotope labeled compound ($^{13}$C-Vemurafenib) shows a competitive exchange of Vemurafenib to i-Vemurafenib, a substitution that provides evidence of specific and selective drug binding. The control tissue in this case does not have any measurable drug binding (not shown).

FIG. 8 (A) shows an image capture with Vemurafenib signal response (m/z 383.1) from the tissue section where 100 nM Vemurafenib was administered within the tissue. The tissue (A) section is a negative control tissue from a patient (patient 1) lacking the V600F BRAF mutation in the BRAF target protein. FIG. 8 (B) shows an image capture for a patient (patient 2) with the V600E mutation in BRAF target protein, with Vemurafenib signal response (m/z 383.1) from the tissue section where 100 nM Vemurafenib was administered within the tissue. FIG. 8 (C) shows an image capture with $^{13}$C-Vemurafenib signal response (m/z 389.1) from the tissue section of patient 2 (with the V600E mutation in BRAF target protein) where 100 nM Vemurafenib and 1 µM $^{13}$C-Vemurafenib was administered within the tissue outcompeting the 100 nM Vemurafenib.

Similarly, FIG. 9 (A) shows an image capture for a patient (patient 3) with the V600E mutation in BRAF target protein, with Vemurafenib signal response (m/z 383.1) from a cell of the tissue section where 100 nM Vemurafenib was administered within the tissue. FIG. 9 (B) is a negative control tissue from a patient (patient 4) lacking the V600F BRAF mutation in the BRAF target protein, and shows an image capture with Vemurafenib signal response (m/z 383.1) from a cell of the tissue section where 100 nM Vemurafenib was administered within the tissue. FIG. 9 (C) shows an image capture for a patient (patient 3) with the V600E mutation in BRAF target protein, with $^{13}$C-Vemurafenib signal response (m/z 389.1) from a cell of the tissue section where 100 nM Vemurafenib and 1 µM $^{13}$C-Vemurafenib was administered within the tissue, outcompeting the 100 nM Vemurafenib.

The competitive exchange of Vemurafenib to i-Vemurafenib provides evidence of specific and selective drug binding. Also, the competitive exchange may provide even more information. In FIGS. 10 (A) to (D), a Co-incubation titration experiment is shown. FIG. 10 (A) shows an image capture with $^{13}$C-Vemurafenib signal response (m/z 389.1) from a cell of the tissue section where 100 nM Vemurafenib was administered within the tissue. FIG. 10 (B) shows an image capture with $^{13}$C-Vemurafenib signal response (m/z 389.1) from a cell of the tissue section where 1 µM Vemurafenib was administered within the tissue. FIG. 10 (C) shows an image capture with $^{13}$C-Vemurafenib signal response (m/z 389.1) from a cell of the tissue section where 10 µM Vemurafenib was administered within the tissue. Finally, FIG. 10 (D) shows an image capture with $^{13}$C-Vemurafenib signal response (m/z 389.1) from the tissue section where 100 µM Vemurafenib was administered within the tissue. The isotope labeled compound ($^{13}$C-Vemurafenib) additions shows a competitive exchange of Vemurafenib to i-Vemurafenib, a substitution that provides evidence of specific and selective drug binding. The $^{13}$C-Vemurafenib signal response is summarized in table 1 below.

TABLE 1

Competitive binding of $^{13}$C-Vemurafenib vs. Vemurafenib.

| Conc-isotope | Isotope Signal | Background |
|---|---|---|
| 100 µM | 259400 | 622 |
| 10 µM | 29870 | 268 |

TABLE 1-continued

Competitive binding of $^{13}$C-Vemurafenib vs. Vemurafenib.

| Conc-isotope | Isotope Signal | Background |
|---|---|---|
| 1 µM | 3233 | 323 |
| 0.1 µM | 326 | 165 |

The binding of $^{13}$C-Vemurafenib is increasing with increasing levels of administration. This clearly indicate the linear relationship in-between the $^{13}$C-Vemurafenib drug concentration and the binding to the cancer cells, with a background of Vemurafenib, as shown in Table 1. The clear cut specificity of competitive binding proves the specificity of the drug binding to the cancer cells and protein target, and the signal/concentration relationship can be used to calculate kinetic binding characteristics for the ligand and/or metabolite and/or target receptor.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method of determining the specific binding of a ligand reversibly binding to a binding site in a tissue sample using displacement competitive inhibition, the method comprising incubating an unlabeled ligand in the absence of a labeled ligand on a first tissue specimen, incubating the unlabeled ligand in the presence of a labeled ligand on a second tissue specimen, the first and the second tissue specimens being adjacent sections of specimen; and subsequently visualizing ligand localisation using MALDI imaging mass spectrometry in the first and second tissue specimen, respectively.

2. The method according to claim 1, wherein the labeled ligand is an isotope-labeled ligand.

3. The method according to claim 2, wherein the isotope-labeled ligand is a deuterium labeled ligand, or a $^{13}$C-isotope labelled ligand.

4. The method according to claim 1, wherein the molar concentration of labeled ligand is higher than the molar concentration of the unlabeled ligand during displacement competitive inhibition.

5. The method according to claim 1, wherein the molar concentration of labeled ligand is 5 to 10 000-fold higher than the molar concentration of the unlabeled ligand during displacement competitive inhibition.

6. The method according to claim 1, wherein the unlabeled ligand is of nanomolar concentration and the labeled ligand is of micromolar concentration.

7. The method according to claim 1, wherein the ligand and labeled ligand are homologs.

8. The method according to claim 1, wherein the localization of a target protein and the -binding is confirmed by co-localization.

9. The method according to claim 1, wherein ligand and/or labeled ligand are quantified using MALDI imaging mass spectrometry.

10. The method according to claim 1, comprising incubating said unlabeled ligand with at least two different concentrations of labeled ligand on adjacent sections of tissue specimens.

11. The method according to claim 10, wherein the method comprises using a titration of different labeled ligand concentrations.

12. The method according to claim 10, wherein kinetic binding characteristics for the ligand and/or metabolite and/or target receptor are calculated from binding data.

13. The method according to claim 12, where in the kinetic binding characteristics are $K_d$, $K_i$, and/or IC50.

14. A method according to claim 1, wherein the ligand is added to the second tissue sample first, at one time point, and the labelled ligand is added at a later time, at a second time point.

15. The method according to claim 1, wherein the ligand is Vemurafenib and the labeled ligand is $^{13}$C-Vemurafenib.

* * * * *